United States Patent
Kondou et al.

(10) Patent No.: US 7,374,938 B2
(45) Date of Patent: May 20, 2008

(54) PROCESS FOR PRODUCING NON-CELLULOSIC CALLOSE FIBER BY PLANT PROTOPLAST AND CALLOSE FIBER

(75) Inventors: Tetsuo Kondou, Ibaraki (JP); Jun Magoshi, Ibaraki (JP); Hisashi Abe, Ibaraki (JP); Hamako Sasamoto, Ibaraki (JP)

(73) Assignees: Japan Science and Technology Corporation, Saitama (JP); National Institute of Agrobiological Sciences, Ibaraki (JP); Forestry and Forest Products Research Institute, Ibaraki (JP)

( * ) Notice: Subject to any disclaimer, the term of this patent is extended or adjusted under 35 U.S.C. 154(b) by 676 days.

(21) Appl. No.: 10/333,225

(22) PCT Filed: Mar. 30, 2001

(86) PCT No.: PCT/JP01/02818

§ 371 (c)(1),
(2), (4) Date: Mar. 13, 2003

(87) PCT Pub. No.: WO02/08441

PCT Pub. Date: Jan. 31, 2002

(65) Prior Publication Data

US 2003/0157663 A1    Aug. 21, 2003

(30) Foreign Application Priority Data

Jul. 21, 2000    (JP) ............... 2000-220419

(51) Int. Cl.
*A01H 4/00*    (2006.01)
*C12P 19/04*    (2006.01)
(52) U.S. Cl. ..................... 435/421; 435/101
(58) Field of Classification Search ............. None
See application file for complete search history.

(56) References Cited

OTHER PUBLICATIONS

Him et al., Biosynthesis of (1—>3)-B-D-glucan (callose) by detergent extracts of a microsomal fraction from *Arabidopsis thaliana*, Eur. J. Biochem. 268, 4628-4638, (2001).*
Pyo et al., Korean Journal of Botany, 32(4), pp. 215-226, 1989.*
Kauss et al., Planta. vol. 178, pp. 385-392, 1989.*
Schaeffer et al., Plant Physiol.. vol. 94, pp. 13-19, 1990.*
Biology-Online, definition of Callose, [online], Retrieved from the Internet:Oct. 10, 2005, <URL:http://www.biology-online.org/dictionary/callose>.*
Kauss et al. Induced Ca2+ uptake and callose synthesis in suspension-cultured cells of *Catharanthus roseus* are decreased by the protein phosphatase inhibitor okadaic acid *Physiolgia plantarum* 81:309-312. (1991).*
Fukumoto et al. Planta 223(1): 40-45 (Dec. 2005).*
Potrykus et al. Molecular and General Genetics 199: 183-188 (1985).*
H. Kauss et al., "The degrees of polymerization and N-acetylation of chitosan determine its ability to elicit callose formation in suspension cells and protoplasts of *Catharanthus roseus* ", Planta, vol. 178, pp. 385 to 392, 1989.
B.S. Pyo, et al., "Effects of calcium and polyamine on callose contents in carrot suspension cultured cells", Korean Journal of Botany, 32 (4), pp. 215 to 226, 1989.
Holly J. Schaeffer et al., "Aluminum Ions Induce Oat Protoplasts to Produce an Extracellular (1 → 3) β-D-Glucan", Plant Physiol. vol. 94, pp. 13 to 19, 1990.
Masako Osumi et al., "Dynamics of Cell Wall Formation in Fission Yeast, *Schizosaccharomyces pombe* ", Fungal Genetics and Biology, vol. 24, pp.178 to 206, 1998.

* cited by examiner

*Primary Examiner*—David T Fox
(74) *Attorney, Agent, or Firm*—Wenderoth, Lind & Ponack, L.L.P.

(57) ABSTRACT

A method for producing non-cellulosic callose fiber by using plant protoplast, which imposes less burden to the environment with reduced energy consumption compared to conventional natural fibers is provided; it comprises the addition of an inorganic ion to a plant protoplast cultivation system, which leads the plant protoplast to produce non-cellulosic callose fiber.

1 Claim, 3 Drawing Sheets

PROCESS FOR PRODUCING NON-CELLULOSIC CALLOSE FIBER BY PLANT PROTOPLAST AND CALLOSE FIBER

This application is a national stage application of International Application No. PCT/JP01/02818, filed Mar. 30, 2001.

TECHNICAL FIELD

The invention of the present application relates to a method for producing non-cellulosic callose fiber using plant protoplast and a callose fiber.

BACKGROUND ART

Fiber materials such as continuous fibers and staple fibers are indispensable in various social and industrial fields. Currently, natural cellulose fibers, regenerated cellulose fibers such as rayon and tensel, and synthetic fibers manufactured by petrochemicals are mainly used as such fiber materials.

However, synthetic fibers are problematic in that they use non-regenerative petroleum resources; also, environmental concerns such as the consumption of large amounts of energy for the preparation of raw materials from petroleum and for the processing of such materials, as well as the problem of waste disposal exist.

On the other hand, although natural cellulose fiber and, regenerated cellulose fiber are expected to support a petroleum-free industry, since such fibers utilize natural products originating from plants, production processes of natural fibers are not necessarily energy-conserving, because rayon and tensel are manufactured by regenerating dissolved cellulose into fibers.

Since means for producing fiber materials with little energy is hoped for in the 21st century, where harmonization of society and environment is expected, novel technical approaches that can solve the problems in the production of natural and regenerative cellulose are urgently called for.

The invention of the present application has been made in view of the above circumstances, and the object of the present invention is to provide a method for producing novel fiber materials with little environmental load and low energy consumption than conventional methods of producing natural fibers.

DISCLOSURE OF THE INVENTION

As a means to solve the above problems, the present invention firstly provides a method for producing non-cellulosic callose fiber from plant protoplast, comprising adding inorganic ions to a plant protoplast cultivation system, thereby making the plant protoplast produce non-cellulosic callose fiber.

Further, the present invention provides secondly, the method for producing non-cellulosic callose fiber, wherein the concentration of the inorganic ions is in the range of 50 to 400 mM, thirdly, the method for producing non-cellulosic callose fiber, wherein the pH value of the cultivation system is in the range of 2 to 6.5, and forthly, the method for producing non-cellulosic callose fiber, wherein the inorganic ions are divalent ions.

Also, the invention of the present application fifthly provides a non-cellulosic callose fiber comprising $\beta$-1,3-glucan chains, and sixthly, such callose fiber produced from plant protoplast.

The invention of the present application has been completed based on the following discovery obtained by the present inventors.

Plant protoplast usually forms cell wall, mainly cellulose. However, when inorganic ions are added to the protoplast cultivation system, protoplast produces giant non-cellulosic fibers towards the exterior of the cell wall by suppressing normal cell division to a minimum level, and the fiber produced is a callose fiber composed of $\beta$-1,3-glucan chains that have not been known to form continuous fibers; this is a completely new knowledge.

Although the role of calcium ions ($Ca^{2+}$) in plant cells has been considered important, until now, it was noticed only in the field of plant physiology. That is, $Ca^{2+}$ was considered to "exist by ionic adsorption in the apoplast crevices such as the cell wall and cytoplasm, and its rate of intake and concentration are both low. The cell maintains the level of $Ca^{2-}$ as low as possible". The effect of $Ca^{2-}$ on the secondary metabolism such as cell wall synthesis has not been investigated. The same was true not only for the effects of $Ca^{2+}$ but also for the effects of other ions.

However, it is important to investigate the effect of ions such as $Ca^{2+}$ ion on the secondary metabolism (cell wall synthesis) in plant to clarify the conformation construction system of natural polymers. The above-described novel findings were obtained by the inventors of the application in the process of such investigation.

The invention of the present application, which enables the production of callose fiber from plant protoplast provides a production system that consumes less energy compared to synthetic fibers that consumes large amounts of energy, because the cells produce the fiber directly. The method also gives less environmental load and consumes less energy as compared to methods of producing natural fiber that require the steps of pulping, refining, dissolution and spinning. The method for producing callose fiber of the present invention is a basic proposal for an energy-conserving means for producing various materials.

BEST MODE FOR CARRYING OUT THE INVENTION

Figure 1:
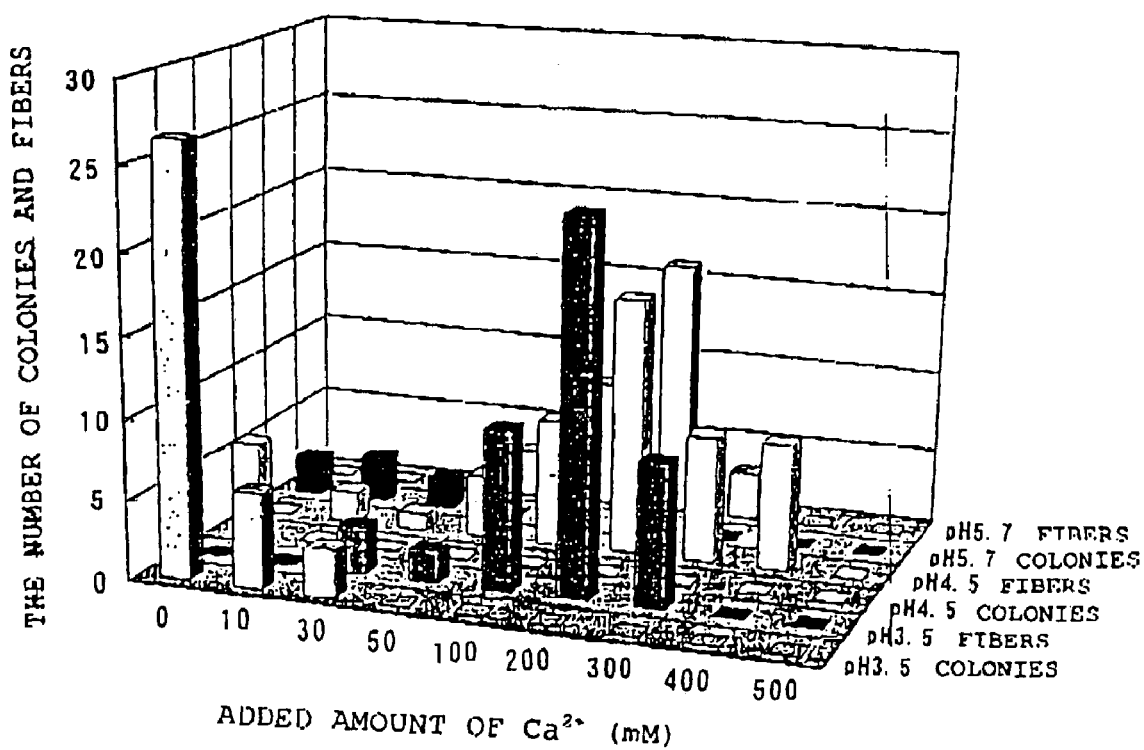
FIG. 1 shows the production of callose fiber by the addition of $Ca^{2+}$ in Example 1 of the present application.

Characteristics of the invention of the present application are as described above; hereinafter, further embodiments of the invention will be described.

According to the present invention, the protoplast produces callose fiber as a giant non-cellulosic fiber toward the exterior of the cell wall when inorganic ions are added to the plant protoplast cultivation system and normal cell division of the protoplast that is capable of cell division is suppressed to a minimum level. In the present invention, protoplasts derived from various plants may be used as the plant protoplast, and conventional cultivation systems may be used.

Specifically, broad-leaved trees and needle-leaved trees such as white birch and larch, which are readily available and easily grown, are suitable. Further, as the cultivation system, systems such as MS (Murashige and Skoog's;

Murashige, T. Skoog, F., Physiol, Plant, 15, 473-497 (1962)), liquid basal medium and their dilution containing various hormones may be used; those containing compounds such as mannitol, sucrose, naphthalene acetic acid and benzyl adenine may be exemplified.

In the present invention, inorganic ions are added to the cultivation system and their concentrations may vary depending on the type of inorganic ions used; generally, concentrations in the range of 50 to 500 mM ire preferable, and more preferable are concentrations in the range of 50 to 400 mM. Production of colonies is predominant over the production of fibers under concentrations of less than 50 mM, while production of the fiber cannot be expected under concentration exceeding 500 mM.

As the inorganic ions to be added, cations of alkali metals, alkali earth metals and transition metals such as Ca, Mg, Ba, Sr, Na, K, Mn, Ti, Zr, Mo and W are preferable. Among them, divalent cations such as $Ca^{2+}$ and $Mg^{2+}$ are suitable. $Ca^{2+}$ is especially effective for the production of the callose fiber of the present invention. The inorganic ions may be added to the cultivation system as chlorides and carbonates.

The preferable pH range of the cultivation system is between 2 to 6.5. For example, for $Ca^{2+}$, a pH value in the range of 3 to 6 is suitable. Alkalis such as KOH and acids such as HCl may be added for pH adjustment. The cultivation temperature is usually selected around the range of 10 to 35° C.

The fiber produced by the method of the present invention is different from cellulose, which consists of β-1,4-glucan chains and constitute the plan cell wall and have been used as natural fiber materials; it is composed of callose, which consists of β-1,3-glucan chains. The properties of callose as fibers differ from those of conventional cellulose fibers, because callose has a helical conformation while cellulose takes a linear chain conformation.

The callose fiber of the present invention is a long filament with a width of several micrometers and is soluble in alkali solutions. Since the callose fiber is a substance with a helical structure consisting of β-glucose, its application is not restricted to those areas where the cellulose fiber has been used; a wide range of application such as edible fibers, film and microcapsules as well as medical fibers may be expected. Of course, composites with other fibers such as cellulose and other substances may be devised for applications in particular fields.

The invention of the present application is described in further detail with reference to the following Examples. The present invention should not be restricted by these examples.

EXAMPLE

Example 1

The protoplasm of white birch (*Betulaplatyphylla* var *japonica*) was cultivated, and callose fibers were produced by adding $Ca^{2-}$ and $Mg^{2+}$ as the inorganic ions, in the form of $CaCl_2$ and $MgCl_2$, at various pH values and ion concentrations. The pH values were adjusted using KOH and HCl before autoclave sterilization at 121° C. for 20 minutes.

The following reagent and hormones were added to a medium with half the strength of MS liquid essential medium:

| | |
|---|---|
| 0.6 M | mannitol |
| 0.09 M | sucrose |
| 1 μM | naphthalene acetic acid (NAA) |
| 10 μM | benzyl adenine (BA) |

Figure 2:
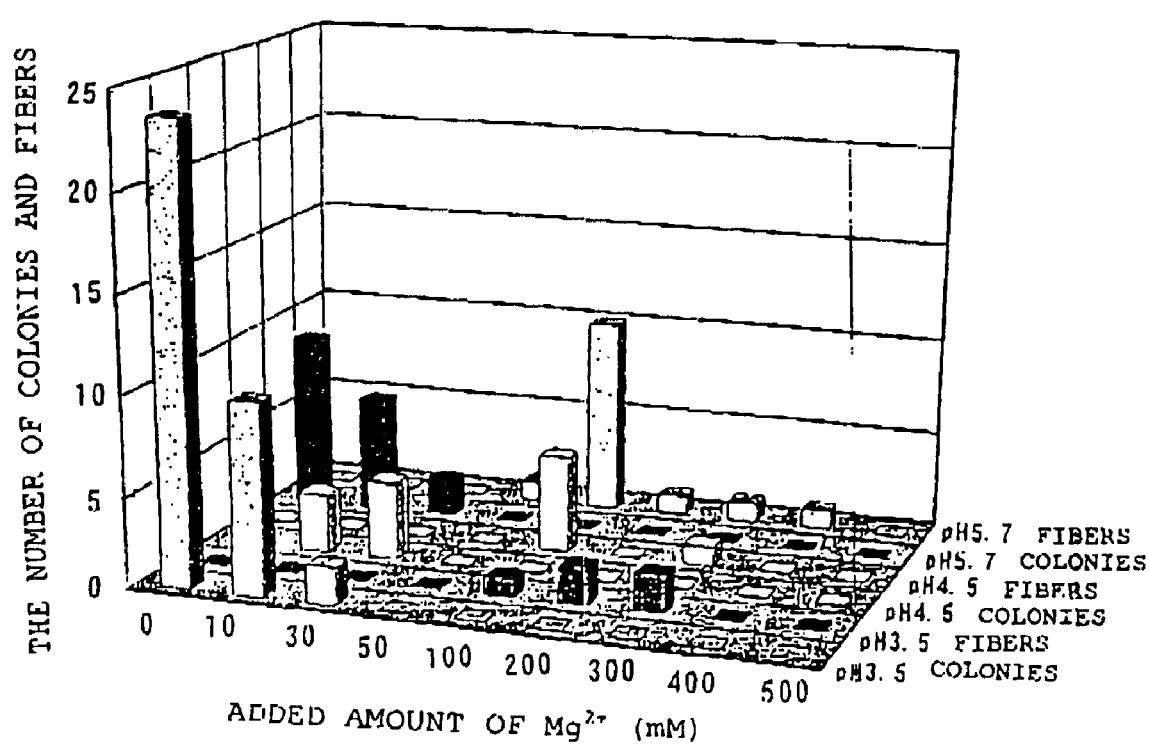
FIG. 2 shows the production of callose fiber by the addition of $Mg^{2-}$ in Example 1 of the present invention.

The results of fiber and colony production are shown in FIG. 1 (for $Ca^{2-}$) and FIG. 2 (for $Mg^{2+}$). The results in FIG. 1 show that callose fiber production was evident under $Ca^{2+}$ concentratiosn of 100 to 400 mM at pH 3.5 to 5.7, particularly under a $Ca^{2+}$ concentration of 200 mM at pH 3.5 to 4.5.

Further, FIG. 2 shows that callose fibers were favorably produced under $Mg^{2+}$ concentrations of 100 to 400 mM at pH $^{3.5}$ to 5.7, particularly under a Mg2+ concentration of 100 mM at pH 4.5 to 5.7.

Example 2

The protoplast used in Example 1 was cultivated under a $Ca^{2+}$ concentration of 200 mM with pH of 3.5 to 4.5 for 3 months. Production of giant fibers was confirmed as indicated in the fluorescence micrograph of FIG. 3.

Figure 3:
FIG. 3 shows a fluorescence micrograph of the fiber produced in Example 2 of the present application.

FIG. 3 shows the fluorescence micrograph of the fiber after staining with calcofluorol. The fiber was identified as callose consisting of β-1,3-glucan chains by staining, antibody fluorescence staining and enzymatic degradation.

Example 3

The protoplast used in Example 1 was cultivated by adding $Na^+$ ions instead of $Ca^{2+}$ and $Mg^{2+}$ ions. Although less effective than the addition of $Ca^{2+}$ and $Mg^{2+}$ ions, production of callose fibers was confirmed under $Na^+$ concentrations of 50 to 500 mM at pH 3.5 to 5.7, particularly under $Na^+$ concentrations of 200 to 300 mM at pH 3.5 or under the $Na^+$ concentration of 500 mM at pH 5.7.

Example 4

The protoplast of larch (*Larix Kaempfeli*) was cultivated by adding 50 mM of $Mg^{2+}$ and $Ca^{2-}$ ions at pH 3 to 6.5, and the production of giant callose fibers similar to those shown in FIG. 3 was confirmed after several weeks.

INDUSTRIAL APPLICATION

As described in detail above, the following effects were exhibited by the invention of the present application:

(1) Since the cells directly produce the fibers, the present invention is an energy-conserving production system compared to known production systems of synthetic fiber that require large amounts of energy; its environmental load and the amount of energy that is consumed is very small compared to methods for producing natural fibers that include the steps of pulping, refining, dissolution and spinning. The present method provides a basis for the construction of a low energy-type material production system, wherein plant protoplast is used.

(2) The fiber produced is different from cellulose, which consists of β-1,4-glucan chains and constitutes the plant cell wall and has been used as natural fiber materials; it is composed of a substance called callose, which consists of β-1,3-glucan chains. The properties of callose as fibers differ from those of conventional cellulose fibers, because callose has a helical conformation while cellulose takes a linear chain conformation. Hence, its application as fibrous materials maybe expected to expand further.

(3) Callose composed of β-glucose is a continuous fiber of several micrometers in width, and is soluble in alkali solutions. Accordingly, the fiber may be used as edible fibers, films and microcapsules, as well as medical fibers.

The invention claimed is:
1. A method for producing non-cellulosic callose fiber, comprising cultivating birch or larch protoplasts under an $Mg^{2+}$, $Ca^{2+}$ or $Na^+$ ion concentration of 50 to 400 mM at a pH value in the range of 3.5 to 5.7 for several weeks to three months.

UNITED STATES PATENT AND TRADEMARK OFFICE
CERTIFICATE OF CORRECTION

PATENT NO. : 7,374,938 B2 Page 1 of 1
APPLICATION NO. : 10/333225
DATED : May 20, 2008
INVENTOR(S) : Tetsuo Kondo et al.

It is certified that error appears in the above-identified patent and that said Letters Patent is hereby corrected as shown below:

Title page item (12), please change "Kondou et al." to --Kondo et al.--.

Title page item (75), Inventors, please change the first inventor's name from "Tetsuo Kondou" to --Tetsuo Kondo--.

Signed and Sealed this

Eleventh Day of November, 2008

JON W. DUDAS
*Director of the United States Patent and Trademark Office*